United States Patent
Yoo et al.

(10) Patent No.: US 10,172,713 B2
(45) Date of Patent: Jan. 8, 2019

(54) METHOD OF MANUFACTURING PATIENT-CUSTOMIZED TIBIAL ELEMENT

(71) Applicant: CORENTEC CO., LTD., Cheonan-si, Chungcheongnam-do (KR)

(72) Inventors: Oui-Sik Yoo, Seoul (KR); Jae-Won Kim, Seoul (KR)

(73) Assignee: Corentec Co., LTD., Cheonan-si, Chungcheongnam-do (KR)

( * ) Notice: Subject to any disclaimer, the term of this patent is extended or adjusted under 35 U.S.C. 154(b) by 182 days.

(21) Appl. No.: 15/176,840

(22) Filed: Jun. 8, 2016

(65) Prior Publication Data

US 2017/0042684 A1 Feb. 16, 2017

(30) Foreign Application Priority Data

Aug. 10, 2015 (KR) .................. 10-2015-0112483

(51) Int. Cl.
*A61F 2/30* (2006.01)
*A61F 2/38* (2006.01)
*A61F 2/28* (2006.01)

(52) U.S. Cl.
CPC .......... *A61F 2/30942* (2013.01); *A61F 2/389* (2013.01); *A61F 2002/2892* (2013.01); *A61F 2002/3096* (2013.01); *A61F 2002/30616* (2013.01); *A61F 2002/30878* (2013.01); *A61F 2002/30884* (2013.01); *A61F 2002/30948* (2013.01); *A61F 2002/30957* (2013.01); *A61F 2240/004* (2013.01); *A61F 2250/0064* (2013.01)

(58) Field of Classification Search
CPC .... A61F 2002/30616; A61F 2250/0064; A61F 2002/30957; A61F 2240/004; A61F 2002/2892; A61F 2/389; A61F 2002/30878; A61F 2002/30884; A61F 2/30942; A61F 2002/30948; A61F 2240/002; A61F 2002/3096
See application file for complete search history.

(56) References Cited

U.S. PATENT DOCUMENTS

| | | | | |
|---|---|---|---|---|
| 2010/0324692 | A1* | 12/2010 | Uthgenannt | G16H 50/50 623/20.35 |
| 2011/0288669 | A1* | 11/2011 | Sanford | A61B 17/00 700/103 |
| 2013/0024001 | A1* | 1/2013 | Wentorf | A61F 2/389 623/20.32 |
| 2014/0142713 | A1* | 5/2014 | Wright | A61F 2/3859 623/20.21 |
| 2014/0228964 | A1* | 8/2014 | Lew | A61F 2/3859 623/20.18 |
| 2014/0259629 | A1* | 9/2014 | Dion | A61F 2/30942 29/558 |
| 2015/0025645 | A1 | 1/2015 | Cho et al. | |

FOREIGN PATENT DOCUMENTS

KR 10-1184905 A 9/2012

* cited by examiner

*Primary Examiner* — Matthew P Travers
(74) *Attorney, Agent, or Firm* — Workman Nydegger

(57) ABSTRACT

A method of manufacturing a patient-customized tibial element for use in artificial knee joint surgery. A tibial element data table regarding sizes of proximal tibial prostheses is formed. Standard molds able to cover the tibial element data table are manufactured. A standard mold is selected from the standard molds in order to manufacture a patient-customized proximal tibial prosthesis. A proximal tibial prosthesis fitting a patient is formed using the selected standard mold.

9 Claims, 8 Drawing Sheets

FIG. 6

(Unit: mm)

| | | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| Baseplate | ML | 55 | 59 | 61 | 64 | 67 | 70 | 72 | 72 | 74 | 74 | 76 | 81 | 84 | 84 | 86 | 86 |
| | AP | 36 | 38 | 40 | 42 | 44 | 45 | 46 | 48 | 48 | 50 | 50 | 52 | 54 | 56 | 56 | 58 |
| Stem | | 20 | | | | 35 | | | | | 40 | | | | | | |
| Neel | | 1 | | | | | 2 | | | | | | 29.5 | | | | |
| Mold | | 1 | | | | | 2 | | | | | | | 3 | | | | |

(Unit: mm)

| | | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| Baseplate | ML | 55 | 58 | 61 | 64 | 67 | 70 | 72 | 72 | 74 | 74 | 76 | 81 | 84 | 84 | 86 | 86 |
| | AP | 36 | 38 | 40 | 42 | 44 | 45 | 46 | 48 | 48 | 50 | 50 | 52 | 54 | 56 | 56 | 58 |
| Stern | | | | | | 35 | | | | | | | | 40 | | | |
| Keel | | | | 20 | | | | | | 24 | | | | | 29.5 | | |
| Mold | | | | 1 | | | | | 2 | | | | 3 | | | 4 | |

MANUFACTURE STANDARD MOLD — S2
DETERMINE NUMBER OF MOLDS — S21
DETERMINE MOLD SIZE — S22

METHOD OF MANUFACTURING PATIENT-CUSTOMIZED TIBIAL ELEMENT

CROSS-REFERENCE TO RELATED APPLICATIONS

This application claims priority to Korean Application No. 10-2015-0112483, filed Aug. 10, 2015, which application is incorporate herein by specific reference.

BACKGROUND OF THE INVENTION

Field of the Invention

The present invention relates generally to a method of manufacturing a patient-customized tibial element. More particularly, the present invention relates to a method of manufacturing a patient-customized tibial element for use in artificial knee joint surgery, the method including; forming a tibial element data table regarding sizes of proximal tibial prostheses; manufacturing standard molds able to cover the tibial element data table; selecting a standard mold from the standard molds in order to manufacture a patient-customized proximal tibial prosthesis; and forming a proximal tibial prosthesis fitting a patient using the selected standard mold.

Description of the Related Art

A knee joint refers to a joint formed by three bones surrounding a knee, including the femur, tibia, and patella. The knee joint is a key joint supporting the weight of the human body and is related to exercises, such as walking and running, in which legs move through the joint motion.

An articular cartridge is present on the distal end of the femur, and a meniscus is present on the distal end of the tibia. When the cartridge is damaged due to aging or excessive exercise, the bones may directly touch each other, causing acute pain.

When the knee joint is damaged, an artificial knee joint surgery is performed by amputating portions of the femur and the tibia and transplanting an artificial knee joint. The artificial knee joint is transplanted by connecting a femur-engaging member 91 to the distal end of the femur F, fixedly fitting a tibial element 93 to the distal end of the tibia T, and mounting a bearing member 95 on the tibial element 93. FIG. 1 is a view illustrating an artificial knee joint of the related art, disclosed in Korean Patent No. 10-1184905 (Sep. 20, 2012).

The tibial element 93 includes a baseplate 931, a stem 933, and keels 935, and is referred to as a proximal tibial prosthesis. Although every patient has a unit bone structure and shape, proximal tibial prostheses of the related art can be fabricated with limited sizes. It is therefore difficult to obtain satisfactory surgery results. After surgeries, some artificial knee joints cause patients discomfort, or in some worse cases, cause complications to patients since the artificial knee joints do not fit to the patients.

Although a method of preparing as many molds as possible in order to manufacture a proximal tibial prosthesis that fits a patient, excessive labor and cost are required, and it is difficult to manage the large number of molds.

Therefore, there is an urgent need for introducing a technology for a method of forming a customized tibial element fitting each patient.

The information disclosed in the Background of the Invention section is only for the enhancement of understanding of the background of the invention, and should not be taken as an acknowledgment or as any form of suggestion that this information forms a prior art that would already be known to a person skilled in the art.

SUMMARY OF THE INVENTION

Accordingly, the present invention has been made keeping in mind the above problems occurring in the related art, and the present invention is intended to propose a method of manufacturing patient-customized proximal tibial prostheses, the method including: forming a tibial element data table that divides data into groups; manufacturing standard molds according to the groups; molding a standard tibial element using a corresponding standard mold of the standard molds; and cutting the cast standard tibial element, such that a large number of patient-customized proximal tibial prostheses having different sizes can be manufactured using a minimum number of standard molds.

Also proposed is a method of manufacturing a tibial element similar to the joint of a patient by manufacturing the patient-customized proximal tibial prosthesis.

Also proposed is a method of manufacturing a patient-customized proximal tibial prosthesis, in which the widths of keels are determined according to groups categorized in a stem data forming step, whereby the number of required standard molds is minimized.

Also proposed is a method of manufacturing a patient-customized proximal tibial prosthesis, in which a number of required standard molds having different sizes can be manufactured using a minimum number of molds, thereby reducing manufacturing cost.

Also proposed is a method of manufacturing a patient-customized proximal tibial prosthesis, the method including: acquiring patient data; selecting and manufacturing a standard mold, the size of which is greater than but closest to a value of the patient data; and manufacturing a standard tibial element using the standard mold, such that a patient-customized proximal tibial prosthesis is manufactured in a short period of time.

Also proposed is a method of manufacturing a patient-customized proximal tibial prosthesis, the method able to prevent an artificial joint from causing patient discomfort or causing complications to a patient since the artificial joint does not fit to the patient.

In order to achieve the above object, the present invention is realized by embodiments having the following features.

According to an embodiment of the present invention, there is a method of manufacturing a patient-customized tibial element for use in artificial knee joint surgery. The method may include: forming a tibial element data table regarding the sizes of proximal tibial prostheses; manufacturing standard molds able to cover the tibial element data table; selecting a standard mold from the standard molds in order to manufacture a patient-customized proximal tibial prosthesis; and forming a proximal tibial prosthesis fitting a patient using the selected standard mold.

The process of forming the tibial element data table may include: forming baseplate data based on sizes of baseplates; categorizing the baseplate data to form groups and determining the length of a stem representative of each of the groups; and determining the width of a keel representative of each of the groups using the groups categorized in the process of categorizing the baseplate data.

The process of forming baseplate data may include measuring the size of each of the baseplates based on a horizontal length from the inner end to the outer end of the baseplate and a vertical length from the front end to the rear end of the baseplate.

The process of determining the length of the stem may include measuring the length of the stem based on a vertical length from the bottom of the baseplate to the distal end of the stem.

The process of determining the width of the keel representative of each of the groups may include determining the width of the keel representative of each of the groups according to the groups categorized in the process of categorizing the baseplate data or subdividing a specific group of the groups categorized in the process of categorizing the baseplate data into subgroups and determining the width of a keel representative of each of the subgroups.

The process of manufacturing the standard mold may include: determining a number of required standard molds using the tibial element data table formed in the process of forming the tibial element data table; and determining sizes of the required standard molds.

The number of the standard molds determined in the process of determining the number of the required standard molds may be equal to the number of the baseplates, in which stems have the same length and keels have the same width.

The process of determining the sizes of the required standard molds may determine the size of each of the standard molds to be equal to or greater than the size of a greatest baseplate in the baseplate data in which stems have the same length and keels have the same width.

The process of selecting the standard mold may include comparing the tibial element data table regarding the size of the proximal tibial prosthesis with patient data and selecting the standard mold, the size of which is greater than but closest to a value of the patient data, after the process of comparing the tibial element data table.

The method may further include, after the process of manufacturing the standard mold, acquiring data regarding a knee joint of a patient into which the patient-customized proximal tibial prosthesis is to be inserted.

The process of acquiring the data regarding the knee joint of the patient may include: acquiring patient knee joint scanning data by scanning the knee joint of the patient into which the patient-customized proximal tibial prosthesis is to be inserted; and extracting the patient data required for manufacturing of the proximal tibial prosthesis using the acquired patient knee joint scanning data.

According to the above-described and following features, combinations, and relations of use that will be described later, the present invention can obtain the following effects.

According to the present invention, it is possible to manufacture a large number of patient-customized proximal tibial prostheses having different sizes using a minimum number of standard molds by forming a tibial element data table, dividing data into groups, manufacturing standard molds according to the groups, molding a standard tibial element using a corresponding standard mold of the standard molds, and cutting the cast standard tibial element.

In addition, according to the present invention, a tibial element similar to the joint of a patient can be manufactured by manufacturing a patient-customized proximal tibial prosthesis.

Furthermore, according to the present invention, the widths of keels are determined according to groups categorized in the stem data forming step, whereby the number of required standard molds is minimized.

In addition, according to the present invention, a number of required standard molds having different sizes can be manufactured using a minimum number of molds, thereby reducing manufacturing cost.

Furthermore, according to the present invention, a patient-customized proximal tibial prosthesis can be manufactured in a short period of time by acquiring patient data, selecting and manufacturing a standard mold, the size of which is greater than but closest to a value of the patient data, and manufacturing a standard tibial element using the standard mold.

In addition, according to the present invention, since a patient-customized proximal tibial prosthesis is manufactured, it is possible to prevent an artificial joint from causing patient discomfort or causing complications to a patient since the artificial joint does not fit to the patient.

BRIEF DESCRIPTION OF THE DRAWINGS

The above and other objects, features and advantages of the present invention will be more clearly understood from the following detailed description when taken in conjunction with the accompanying drawings, in which:

FIG. 6 illustrates an exemplary tibial element data table;

DETAILED DESCRIPTION OF THE INVENTION

Reference will now be made in greater detail to a method of manufacturing a patient-customized tibial element according to the present invention in conjunction with the accompanying drawings. In addition, detailed descriptions of known functions and components incorporated herein will be omitted to avoid making the subject matter of the present invention unclear. Unless not specifically defined, all terminologies in the specification should be interpreted based on the general meanings thereof that a person skilled in the art understands. When the general meanings of the terminologies are incompliant with those used in the specification, the terminologies should be interpreted as being defined herein.

In the following description of the invention, one side in the direction of a sagittal plane forming a conceptual central cross-section by which a human body can be divided into the right part and the left part will be referred to as a medial side, and the opposite side will be referred to as a lateral side. In addition, one side in the direction of a coronal plane forming a conceptual central cross-section by which a human body can be divided into the front part and the rear part will be referred to as an anterior side, and the opposite side will be referred to as a posterior side.

In addition, the term "artificial knee joint surgery" is a concept including all of entire replacement surgery, partial replacement surgery, and the like.

Figure 1:
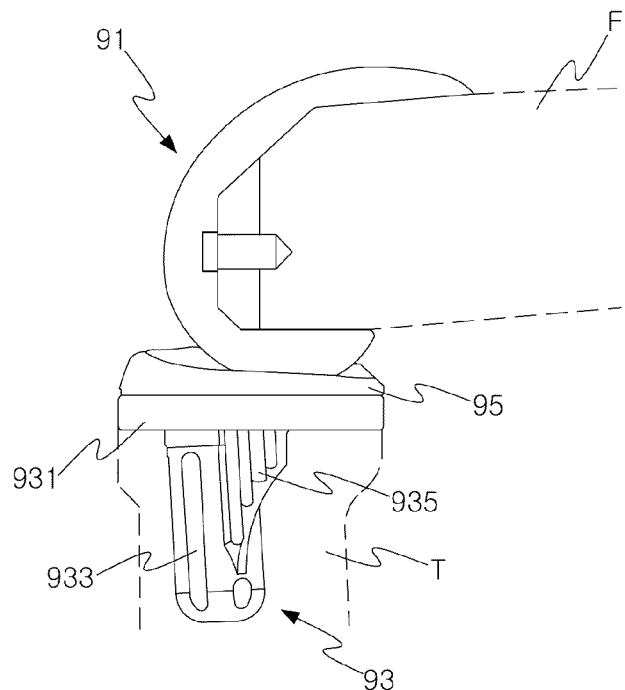
FIG. 1 is a view illustrating an artificial knee joint of the related art.
Figure 2:
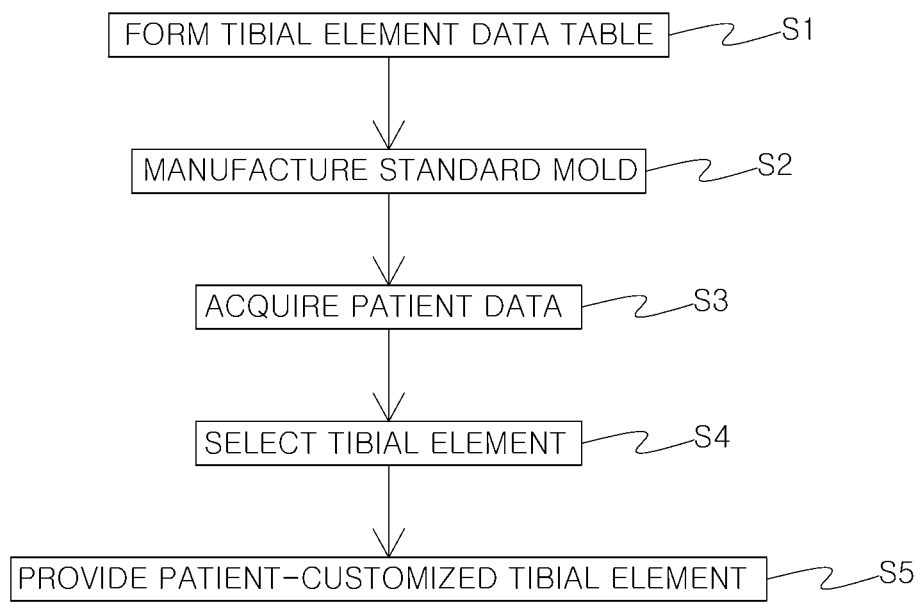
FIG. 2 is a flowchart illustrating a method of manufacturing a patient-customized tibial element according to the present invention.

FIG. 2 is a flowchart illustrating a method of manufacturing a patient-customized tibial element according to the present invention. Referring to FIG. 2, the method of manufacturing a patient-customized tibial element includes step S1 of forming a tibial element data table, step S2 of forming standard molds, step S3 of acquiring patient data, step S4 of selecting a tibial element, and step S5 of providing a patient-customized tibial element.

The step S1 of forming a tibial element data table is a step of forming a data table regarding the dimensions of a proximal tibial prosthesis for an artificial knee joint surgery. Although a variety of methods may be used to measure the dimensions of the proximal tibial prosthesis, it is preferable that the dimensions of the proximal tibial prosthesis include the size of a baseplate 10, the length of a stem 30, and the widths of keels 50 (see FIGS. 3A to 3D).

FIGS. 3A to 3D illustrate a proximal tibial prosthesis. In FIGS. 3A to 3D, FIG. 3A is a perspective view of the proximal tibial prosthesis. The proximal tibial prosthesis includes the stem 30 inserted into a tibia, the keels 50 ensuring the stem 30 is reliably fixed, and the baseplate 10 disposed on top of the stem 30 and the keels 50.

Figure 3A:
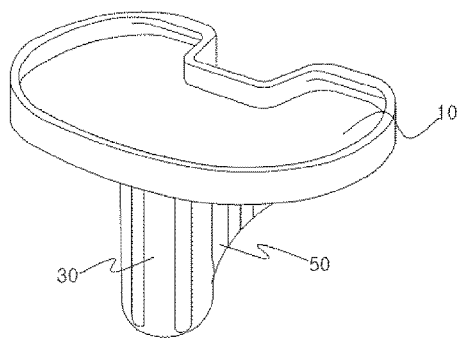
FIGS. 3A to 3D illustrate a proximal tibial prosthesis.
Figure 3B:
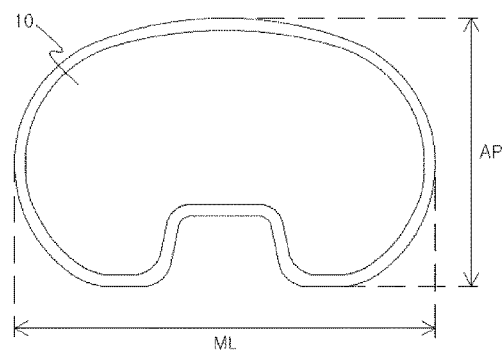
Figure 3C:
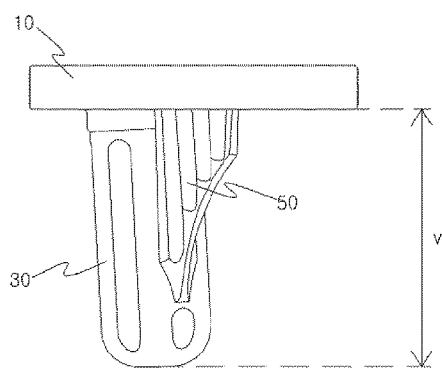
Figure 3D:
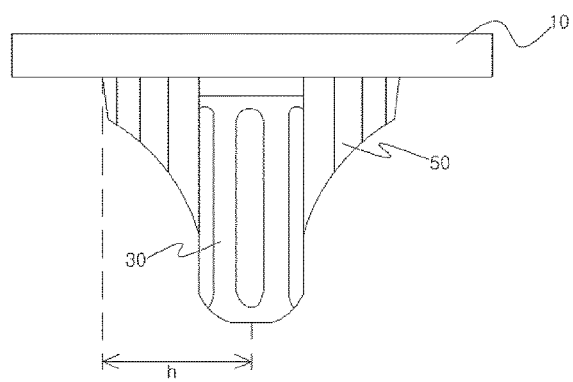

The dimensions of the baseplate 10 are measured as a horizontal length ML from the inner end to the outer end of the baseplate 10 and a vertical length AP from the front end to the rear end of the baseplate 10 when viewed from the plane thereof (see FIG. 3B). The length of the stem 30 is measured as a vertical length v from the bottom of the baseplate 10 to the distal end of the stem 30 (see FIG. 3C). The width of a keel 50 is measured as a horizontal length h from the central axis of the stem 30 to the outermost portion of the keel 50 abutting the bottom of the baseplate 10 (see FIG. 3D). Since FIGS. 3A to 3D more specifically illustrate the present description, it is preferable that the size of the baseplate 10, the length of the stem 30, and the width of the keel 50 are determined based on the illustrations of FIGS. 3A to 3D.

Figure 4:
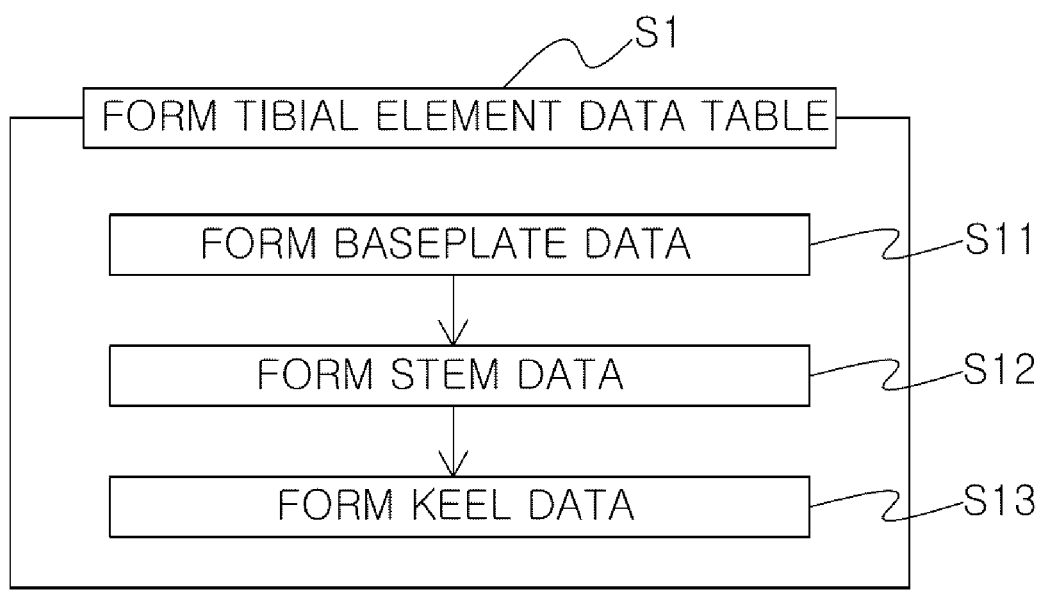
FIG. 4 is a flowchart illustrating the step of forming a tibial element data table, presented in FIG. 2.

FIG. 4 is a flowchart illustrating the step of forming a tibial element data table, presented in FIG. 2. Referring to FIG. 4, the step S1 of forming a tibial element data table includes a baseplate data forming step S11, a stem data forming step S12, and a keel data forming step S13.

The baseplate data forming step S11 is a step of forming data based on the size of the baseplate 10, in which the horizontal length ML from the inner end to the outer end and the vertical length AP from the front end to the rear end of the baseplate 10 are factors to be measured. The standard, based on which the data of baseplates 10 are determined, is not significantly limited, i.e. differences between adjacent data are not required to be set to any constant value, or the differences are not required to be equal to or more than any value or be equal to or less than any value. As presented in FIG. 6, it is possible to set the number of data, values of data, and differences between adjacent data to any values by dividing the size of the baseplate 10 into the horizontal length ML and the vertical length AP.

FIG. 6 illustrates data of sixteen baseplates 10. It can be appreciated that the data of the baseplates 10 are composed in specific ranges of the horizontal length ML and the vertical length AP, in which the horizontal length ML is limited to the range from 55 mm to 86 mm, and the vertical length AP is limited to the range from 36 mm to 58 mm.

Describing the relationship between adjacent data, in the range from the first baseplate 10 to the fifth baseplate 10, the horizontal length ML between the adjacent baseplates increases by 3 mm, and the vertical length AP between the adjacent baseplates regularly increases by 2 mm. However, it can be appreciated that the increment of the horizontal length ML between the fifth baseplate 10 and the sixth baseplate 10 is changed, i.e. the difference in the horizontal length ML is 3 mm, and the difference in the vertical length AP is 1 mm. It can also be appreciated that the increment of the horizontal length ML between the sixth and seventh baseplates 10 is changed, i.e. the difference in the horizontal length ML is 2 mm.

As illustrated in the foregoing example, the data of the baseplate 10 may be determined randomly. However, it is preferable in the manufacture of a patient-customized proximal tibial prosthesis that the average size of human knee joints is statistically determined and the difference between adjacent data in ranges close to the average is reduced.

The stem data forming step S12 is a step of categorizing the data of baseplates 10 into groups and determining the length of a stem 30 representative of each group of data. Describing with reference to FIG. 5, it is assumed that data of a total of n number of baseplates 10 are formed in the baseplate data forming step S11. Afterwards, a total of m number of groups is formed by grouping adjacent data from among the data of n number of baseplates 10, and the length of a stem 30 representative of each group is determined such that each group has a common single stem length. Since a total of m number of groups is formed as described above, a total of m number of representative lengths of stems 30 is produced.

Describing in detail with reference to FIG. 6, in the baseplate data forming step S11, sixteen data are formed depending on the horizontal length ML and the vertical length AP of the baseplates 10. Based on these data, one group is famed by binding data from the first baseplate 10 to the ninth baseplate 10, and another group is formed by binding data from the tenth baseplate 10 to the sixteenth baseplate 10. It can be appreciated that a stem 30 having a length of 35 mm is disposed in the group formed by binding data from the first baseplate 10 to the ninth baseplate 10 and a stem 30 having a length of 40 mm is disposed in the other group formed by binding data from the tenth baseplate 10 to the sixteenth baseplate 10.

That is, groups are formed by binding data based on the data table formed in the baseplate data forming step S11, and the length of a stem representative of each group is determined, such that the data of baseplates 10 in the same group have the same length of stems 30.

Since this categorization is an example, groups may be formed differently from the present embodiment in which one group includes the first to ninth baseplates 10. For example, a first group may be formed by binding the first to fifth baseplates 10, and a first group may be formed by binding the sixth to tenth baseplates 10. Differently from the illustration of FIG. 5, the length of the stem 30 representative of the data from the first to ninth baseplates 10 may be set to 38 mm instead of 35 mm. In this manner, a variety of embodiments may be considered.

The keel data forming step S13 is a step of determining the width of a keel 50 representative of each group based on the groups categorized in the stem data forming step S12. This will be described with reference to FIG. 5. Data of a total of n number of baseplates 10 are formed in the baseplate data forming step S11, a total of m number of groups is formed by binding adjacent data from among the data of the total of n number of baseplates 10, and then the representative length of a stem 30 of each group is determined such that data of baseplates 10 bound in each group have a common length of stem 30. The number of types of lengths of stems 30 representative of the groups is equal to the number (m) of categorized groups.

In contrast, the number of widths of keels 50 formed in the keel data forming step S13 may not be equal to the number of groups categorized in the stem data forming step S12. This is because, although the keel data forming step S13 uses the groups categorized in the stem data forming step S12, data in each group may be divided into subgroups.

Figure 5:
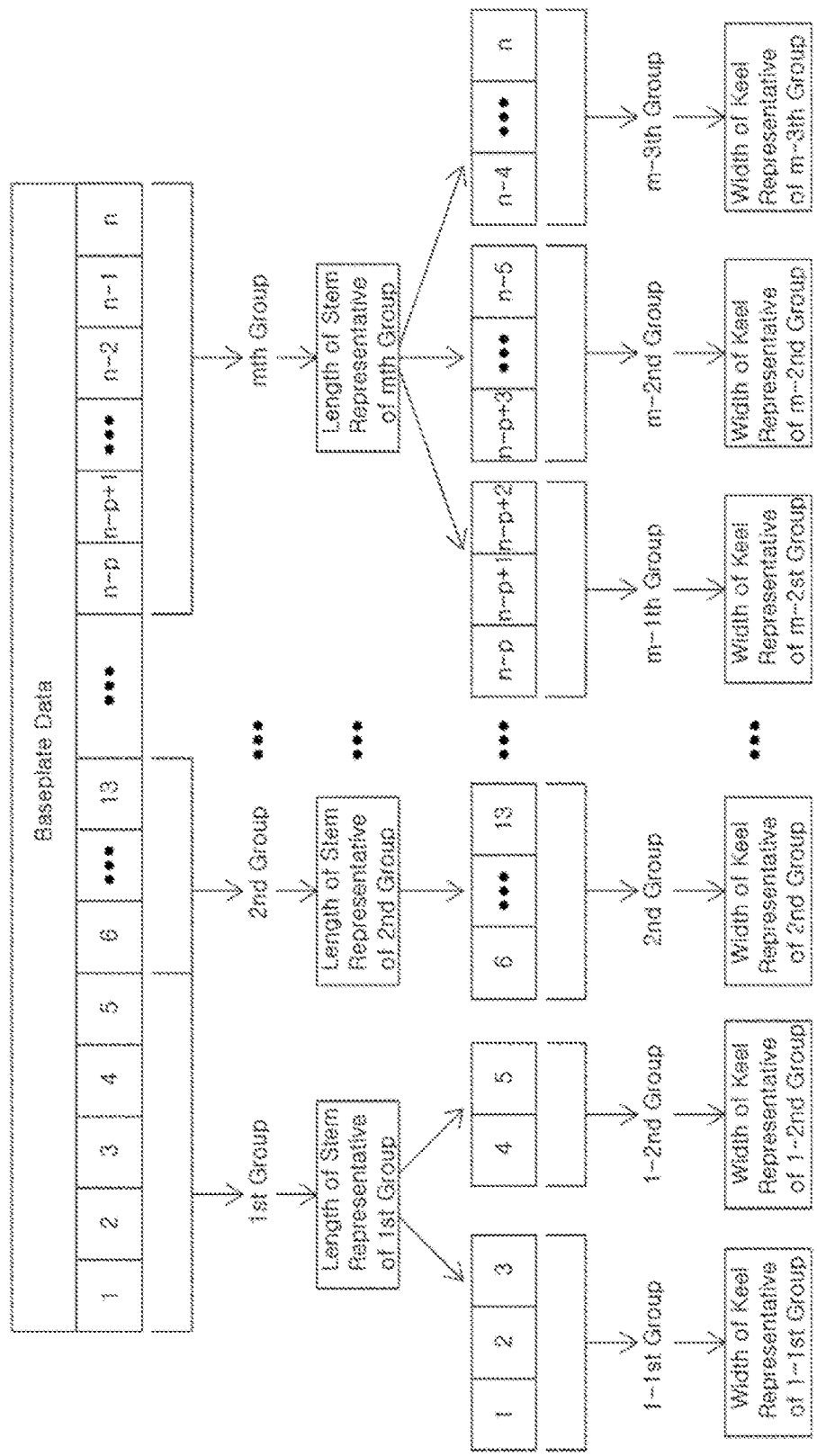
FIG. 5 is a diagram illustrating a process of forming stem data and keel data.

In FIG. 5, the data 1 of the first baseplate 10 to the data 5 of the fifth baseplate 10 form a first group, and the length of the stem 30 representative of the first group is determined. The first group is subdivided into a group 1-1 consisting of the data 1 of the first baseplate 10 to the data 3 of the third baseplate 10 and a group 1-2 consisting of the data 4 of the fourth baseplate 10 and the data 5 of the fifth baseplate 10. In addition, the width of the keel 50 representative of the group 1-1 and the width of the keel 50 representative of the group 1-2 are determined.

Unlike the case in which the group is subdivided, the data 6 of the sixth baseplate 10 to the data 13 of the thirteen baseplate 10 form a second group, and the length of the stem 30 representative of the second group 2 is determined. Based on the categorization of groups, the width of the keel 50 representative of the second group is determined.

That is, after the stem data forming step S12, the keel data forming step S13 can determine the widths of the plurality of keels 50 by subdividing the groups categorized in the stem data forming step S12. This is intended to manufacture a number of proximal tibial prostheses having different sizes using a minimum number of molds. Hereinafter, with reference to FIG. 7, a specific reason therefor will be described.

Figures 7, 8:
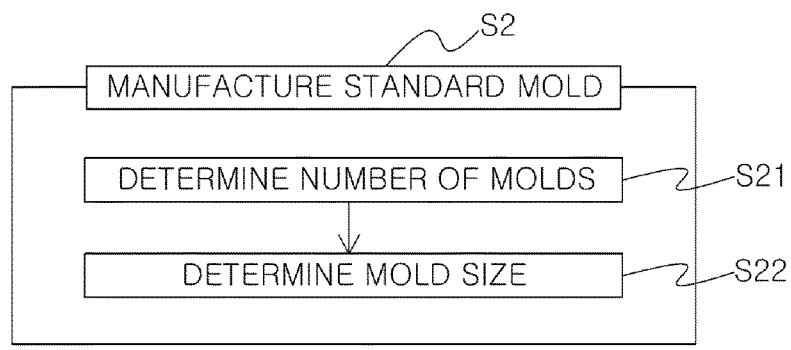
FIG. 7 illustrates another exemplary tibial element data table.
FIG. 8 is a flowchart illustrating the step of manufacturing a standard mold, presented in FIG. 2.

FIG. 7 illustrates another exemplary tibial element data table. Referring to FIG. 7, unlike FIG. 6, data of baseplates 10 are bound to form groups and the width of a keel 50 representative of each group is determined independently using a method the same as the method of determining the lengths of the stems 30 without using the groups categorized in the stem data forming step S12.

According to this embodiment, it can be appreciated that the stem data forming step S12 forms one group by binding data from a first baseplate 10 to a ninth baseplate 10 and another group by binding data from a tenth baseplate 10 to sixteenth baseplate 10, in which the lengths of representative stems 30 of the groups are set to 35 mm and 40 mm, respectively. In order to determine the widths of keels 50 independently from the group categorization, data from the first baseplate 10 to the fifth baseplate 10 are bound into a first group, data from the sixth baseplate 10 to the twelfth baseplate 10 are bound into a second group, and data from the thirteenth baseplate to the sixteenth baseplate 10 are bound into a third group, thereby forming keels 50 having widths 20 mm, 24 mm, and 29.5 mm. In this case, it can be appreciated that four standard molds are required, as will be described later. (A specific description of a method of manufacturing a standard mold will be given later.)

In FIG. 6, the first baseplate 10 to the ninth baseplate 10 are bound into one group, with the stem 30 having a length 35 mm being determined as a representative stem, and the tenth baseplate 10 to the sixteenth baseplate 10 are bound into the other group, with stems 30 having a length 35 mm and a length 40 mm being determined as representative stems. The processing up to this stage is the same as that of the example illustrated in FIG. 7. Keels 50 having widths 20 mm, 24 mm, and 29.5 mm are formed by binding the first to third baseplates 10 into a first group, the fourth to ninth baseplates 10 into a second group, and the tenth to sixteenth baseplates 10 into a third group. In this case, three standard molds are required. It can be appreciated that the example illustrated in FIG. 6 requires only three standard molds to cover the same data of baseplates 10, while the example illustrated in FIG. 7 requires four standard molds.

That is, the widths of the keels 50 belonging to the group categorized in the stem data forming step S12 must be determined in order to minimize the number of standard molds. In other words, when the lengths of the stems 30 are determined in the the groups formed by dividing data based on between the ninth baseplate 10 and the tenth baseplate 10, the width of the keel 50 of the ninth baseplate 10 cannot be determined to be the same as the width of the keel 50 of the tenth baseplate 10. In this case, in each group categorized in the stem data forming step S12, the keels 50 may have different widths. For example, as illustrated in FIG. 6, the first to ninth baseplates 10 belong to a single group in which the length of the stem 30 is 35 mm. However, in this group, the widths of the keels 50 of the first to third baseplates 10 may be determined to be 20 mm, and the widths of the keels 50 of the fourth to ninth baseplates 10 may be determined to be 24 mm.

The step S2 of forming standard molds is a step of manufacturing a standard mold covering the tibial element data table formed in the step S1 of forming a tibial element data table, and includes a mold number determining step S21 and a mold size determining step S22 (see FIG. 8).

The mold number determining step S21 is a step of determining the number of required standard molds using the data table formed in the step S1 of forming a tibial element data table. Referring to the example illustrated in FIG. 6, when the lengths of the stems 30 and the widths of the keels 50 are determined by forming the data of the first to sixteenth baseplates 10 and grouping the baseplates 10, the data of baseplates 10, in which the stems 30 have the same length and the keels 50 have the same width, form a standard mold.

Referring to the example illustrated in FIG. 6, it can be appreciated that the first to third baseplates 10 form standard mold 1 having a stem length of 35 mm and a keel width of 20 mm, the fourth to ninth baseplates 10 foil standard mold 2 having a stem length of 35 mm and a keel width of 24 mm, and the tenth to sixteenth baseplates 10 form standard mold 3 having a stem length of 40 mm and a keel width of 29.5 mm.

Thus, the number of standard molds is determined to be equal to the number of groups of baseplates 10 respectively having the same length of stems 30 and the same width of keels 50.

The mold size determining step S22 is a step of the size of each of required standard molds. Referring to FIG. 6, one group is formed by binding data of baseplates 10 having the same length of stems 30 and the same width of keels 50. In this step, the size of a standard mold of each group is determined to be equal to or greater than the size of a baseplate 10 having the greatest size in each group. It is preferable that the length of the stem 30 and the width of the keel 50 of a standard mold are determined by data formed in the step S1 of forming a tibial element data table, while the size of the baseplate is equal to or greater than the data of the baseplate having the greatest size in each group.

Referring to the example illustrated in FIG. 6, a first group having a stem length of 35 mm and a keel width of 20 mm is formed of the data of the first to third baseplates 10, and standard mold 1 is manufactured based on data 3 having the greatest size in this group, in which the horizontal length ML of the baseplate exceeds 61 mm, the vertical length AP of the baseplate exceeds 40 mm, the length of the stem 30 is 35 mm, and the widths of the keels 50 are 20 mm. A second group having stem length of 35 mm and a keel width of 24 mm is formed of the data of the fourth to ninth baseplates 10, and standard mold 2 is manufactured based on data 9 having the greatest size in this group, the horizontal length ML of the baseplate exceeds 74 mm, the vertical length AP of the baseplate exceeds 48 mm, the length of the stem 30 is 35 mm, and the widths of the keels 50 are 24 mm. In addition, a third group having stem length of 40 mm and a keel width of 29.5 mm is famed of the data of the tenth to sixteenth baseplates 10, and standard mold 3 is manufactured based on data 16 having the greatest size in this group, the horizontal length ML of the baseplate exceeds 86 mm, the vertical length AP of the baseplate exceeds 58 mm, the length of the stem 30 is 40 mm, and the widths of the keels 50 are 29.5 mm.

Through the mold number determining step S21 and the mold size determining step 22, the number of required standard molds and the size of each of the standard molds are determined, such that standards molds are manufactured based on the number and sizes thereof. Materials used for the manufacture of standard molds and manufacturing methods thereof are not specifically limited, and a variety of technologies that is known or is yet to be discovered may be used.

Figure 9:
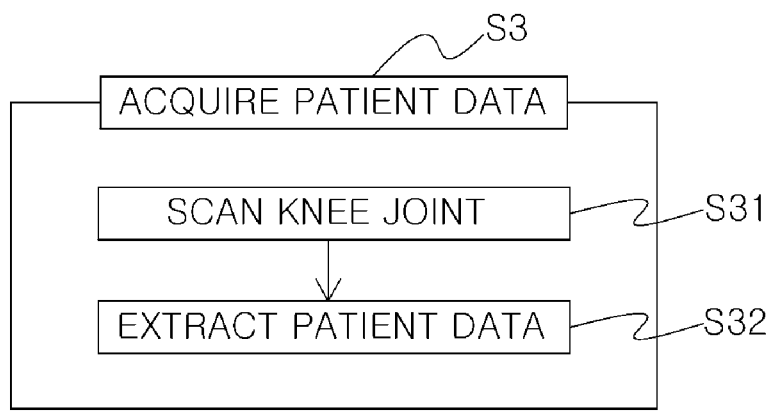
FIG. 9 is a flowchart illustrating the step of acquiring patient data, presented in FIG. 2.

The step S3 of acquiring patient data is a step of acquiring data regarding the knee joint of a patient into which a patient-customized proximal tibial prosthesis is to be inserted, and includes a scanning step S31 and a patient data extracting step S32 (see FIG. 9).

The scanning step S31 is a step of acquiring patient knee joint scanning data by scanning the knee joint of the patient to be subjected to an artificial knee joint surgery. A variety of scanning methods, such as X-ray scanning or computerized tomography (CT), may be used. The scanning is not limited to a specific concept, and a variety of scanning methods that is known or is yet to be discovered may be used.

The patient data extracting step S32 is a step of extracting patient data required for the manufacture of the proximal tibial prosthesis using the patient knee joint scanning data acquired through the scanning step 31. It is preferable that the patient data extracting step S32 may extract the horizontal length ML and the vertical length AP of a proximal tibia, the thickness of a tibia, and the like, corresponding to the values of the tibial element data table formed in the step S1 of forming a tibial element data table.

Figure 10:
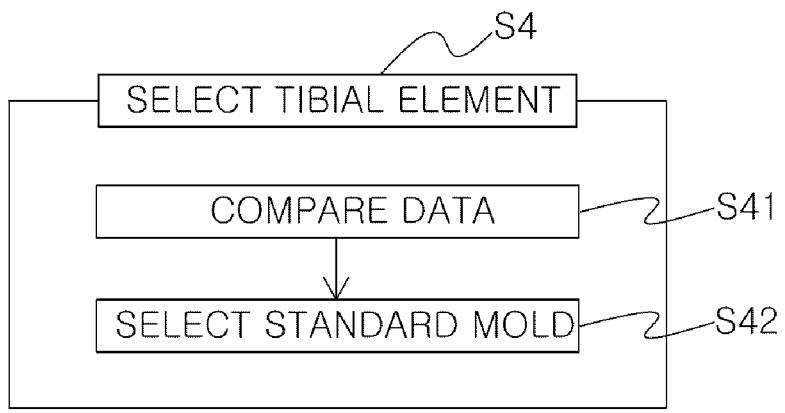
FIG. 10 is a flowchart illustrating the step of selecting a tibial element, presented in FIG. 2.

The step S4 of selecting a tibial element is a step of selecting a standard mold in order to manufacture a patient-customized proximal tibial prosthesis. FIG. 10 is a flowchart illustrating the step of selecting a tibial element, presented in FIG. 2. Referring to FIG. 10, the step of selecting a tibial element S3 includes a data comparing step S41 and a standard mold selecting step S42.

The data comparing step S41 is a step of comparing a tibial element data table regarding the size of a proximal tibial prosthesis with patient data extracted through the patient data extracting step S32. This is the process of comparing the patient data, acquired through measuring the horizontal length ML and the vertical length AP of the proximal tibia, the thickness of the tibia, and the like using X-ray scanning, CT, or the like, with data values in the data table regarding the size of the proximal tibial prosthesis formed through the step S1 of forming a tibial element data table.

The standard mold selecting step S42 is a step of selecting a standard mold, the size of which is greater than and is closest to the patient data, after the data comparing step S41.

Referring to FIG. 6, when the proximal tibia of a patient is measured to have, for example, a horizontal length ML of 74 mm and a vertical length AP of 49 mm, the ninth baseplate 10 and the tenth baseplate 10 may be considered. As will be described later, the process of manufacturing a patient-customized tibial element may include selecting a standard mold, the size of which is greater than the patient data, molding a standard tibial element using the standard mold, and cutting the standard tibial element. In this case, it is preferable that the tenth baseplate 10 is selected. According to the foregoing description, when each group is formed by binding the data of baseplates 10, in which the stems 30 have the same length, and the keels 50 have the same width, the size of each standard mold is set to be equal to or greater than the baseplate 10 having the greatest size of the group. Thus, in some cases, it may be difficult to manufacture a baseplate 10 having a vertical length AP of 49 mm using a standard mold, in which the vertical length AP of the baseplate 10 is 48 mm or greater. Thus, in this example, standard mold 3 is selected.

However, since the baseplate 10 of standard mold 3 has a horizontal length ML of 86 mm or greater and a vertical length AP of 58 mm or greater, when a standard tibial element is manufactured using the standard mold in order to manufacture a patient-customized proximal tibial prosthesis in the above-assumed example, a large amount of the standard tibial element must be cut in order to manufacture a patient-customized tibial element.

Thus, in order to overcome this problem, it is preferable that the average size of the knee joints of people is determined in the step S1 of forming a tibial element data table, and that adjacent data do not belong to different groups in an area close to the average size.

The step of providing a patient-customized tibial element S4 is a step of casting a standard tibial element using the selected standard mold and machining the standard tibial element to manufacture a patient-customized proximal tibial prosthesis.

Figure 11A:
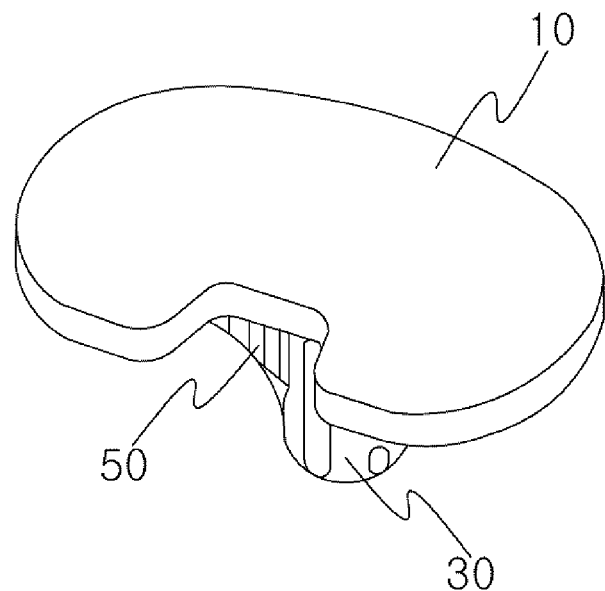
FIGS. 11A and 11B are views illustrating a process of machining a standard tibial element in the step of providing a patient-customized tibial element, presented in FIG. 2.
Figure 11B:
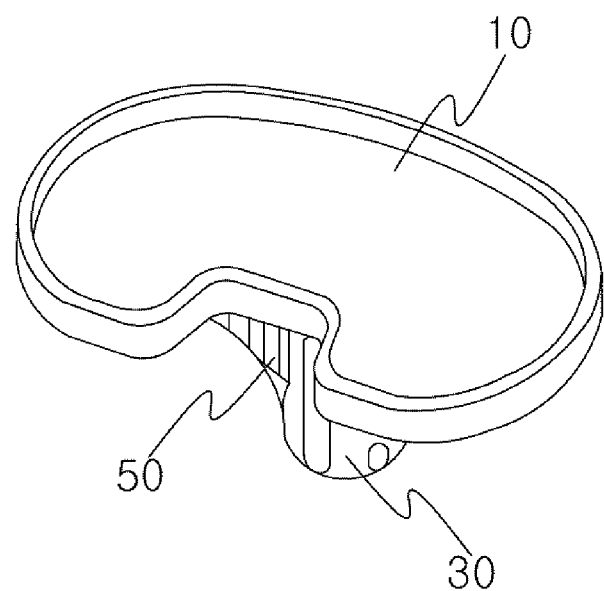

Referring to the example illustrated in FIG. 6, when the proximal tibia of the patient has a horizontal length ML of 73 mm and a vertical length of 47 mm, standard mold 2 is selected in the step S4 of selecting a tibial element, and a standard tibial element is manufactured using standard mold 2. As illustrated in FIG. 11A, a sold baseplate is cut using a machine tool, such as a computerized numerical control (CNC) machine, such that the horizontal length ML is 73 mm and the vertical length is 47 mm. In addition, as illustrated in FIG. 11B, the interior of the solid baseplate is machined, such that a stem having a length of 35 mm and keels 50 having widths of 24 mm are formed, whereby a patient-customized proximal tibial prosthesis is manufactured.

According to the present invention it is possible to manufacture a large number of proximal tibial prostheses having different sizes using a minimum number of standard molds through a series of the process steps as described above. In addition, the above-described process steps can be automatically realized by a computer. The computer can be used in the process of forming a tibial element data table, calculating the number and sizes of required standard molds, extracting required patient data by scanning the knee joint of a patient subjected to an artificial knee joint surgery, selecting a suitable standard mold by comparing the patient data with the formed tibial element data table, manufacturing a standard tibial element using the selected standard mold, and automatically machining the standard tibial element.

The foregoing detailed descriptions have been presented in order to illustrate the present invention. The foregoing descriptions describe the exemplary embodiments of the invention, and a variety of different combinations, modifications, and environments may be used in the present invention. Alterations and modifications are possible within the range of the concept of the invention disclosed herein, within the range equivalent to the foregoing disclosure, and/or within the range of technologies and knowledge of the art. The foregoing embodiments include best modes for embodying the principle of the invention and various changes required in specific fields and uses of the invention are possible. The detailed description of the invention is not intended to limit the invention to the disclosed embodiments. In addition, it should be understood that the appended claims include different forms of embodiment.

What is claimed is:

1. A method of manufacturing a patient-customized tibial element for use in artificial knee joint surgery, the method comprising:
    forming a tibial element data table comprising dimensions of a plurality of different sizes of proximal tibial prostheses, each proximal tibial prostheses having a baseplate, a stem and a keel, the process of forming the tibial element data table comprising categorizing dimensions of the baseplates of the plurality of proximal tibial prostheses into separate groups;
    manufacturing standard molds corresponding to different sizes of the proximal tibial prostheses set forth in the tibial element data table, the process of manufacturing the standard molds comprises:
        determining a number of required standard molds to be manufactured using the tibial element data table, the determined number of required standard molds being equal to a number of the groups of the baseplates of the plurality of different sizes of proximal tibial prostheses in which the stems have a same length and the keels have a same width; and
        determining sizes of the required standard molds;
    selecting a standard mold from the standard molds in order to manufacture a patient-customized proximal tibial prosthesis;
    forming a proximal tibial prosthesis for a patient using the selected standard mold, the process of forming the proximal tibial prothesis including machining the proximal tibial prothesis.

2. The method according to claim 1, wherein the process of forming the tibial element data table comprises:
    forming baseplate data for the baseplates;
    determining a length of the stem for each group of baseplates; and
    determining a width of the keel for each group of baseplates.

3. The method according to claim 2, wherein the process of forming the baseplate data comprises determining a size of each of the baseplates based on a horizontal length from an inner end to an outer end of each baseplate and a vertical length from a front end to a rear end of each baseplate.

4. The method according to claim 3, wherein the process of determining the length of the stem comprises determining the length of the stem based on a vertical length from a bottom of the baseplate to a distal end of the stem.

5. The method according to claim 4, wherein the process of determining the width of the keel for each group of the baseplates further comprises subdividing a specific group of the groups of the baseplates into subgroups and determining a width of a keel representative of each of the subgroups.

6. The method according to claim 2, wherein the process of determining the sizes of the required standard molds determines the size of each of the standard molds to be equal to or greater than a size of a largest baseplate in the baseplate data in which the stems have a same length and the keels have a same width.

7. The method according to claim 6, wherein the process of selecting the standard mold comprises comparing the size of the proximal tibial prosthesis set forth in the tibial element data table with patient data and selecting the standard mold, the size of the standard mold being greater than but closest to a value of the patient data.

8. The method according to claim 7, further comprising, after the process of manufacturing the standard mold, acquiring data regarding a knee joint of a patient into which the patient-customized proximal tibial prosthesis is to be inserted.

9. The method according to claim 8, wherein the process of acquiring the data regarding the knee joint of the patient comprises:
    acquiring patient knee joint scanning data by scanning the knee joint of the patient into which the patient-customized proximal tibial prosthesis is to be inserted; and
    extracting the patient data required for manufacturing of the proximal tibial prosthesis using the acquired patient knee joint scanning data.

* * * * *